United States Patent [19]
Whittaker et al.

[11] Patent Number: 5,267,019
[45] Date of Patent: Nov. 30, 1993

[54] METHOD AND APPARATUS FOR REDUCING FRINGE INTERFERENCE IN LASER SPECTROSCOPY

[75] Inventors: Edward A. Whittaker, Hoboken; Hoi C. Sun, Bloomfield, both of N.J.

[73] Assignee: Consortium for Surface Processing, Inc., Princeton, N.J.

[21] Appl. No.: 767,497

[22] Filed: Sep. 30, 1991

[51] Int. Cl.[5] .................. G01N 21/35; G01N 21/61
[52] U.S. Cl. ................................ 356/437; 250/343; 356/409
[58] Field of Search ............... 356/409, 326, 324, 325, 356/437; 250/343

[56] References Cited

U.S. PATENT DOCUMENTS

| | | | |
|---|---|---|---|
| 4,684,258 | 8/1987 | Webster | 356/409 |
| 4,730,112 | 3/1988 | Wong | 250/343 |
| 4,746,218 | 5/1988 | Lord, III | 356/437 |
| 4,749,276 | 6/1988 | Bragg et al. | 356/246 |
| 4,849,637 | 7/1989 | Cerff et al. | 250/345 |
| 4,883,963 | 11/1989 | Kemeny et al. | 250/339 |
| 4,897,548 | 1/1990 | Dome et al. | 250/343 |
| 4,934,816 | 6/1990 | Silver et al. | 356/409 |
| 4,937,448 | 6/1990 | Mantz et al. | 356/324 X |

OTHER PUBLICATIONS

Silver and Stanton, Optical Interference Fringe Reduction in Laser Absorption Experiments, Applied Optics, vol. 27, No. 10, pp. 1914–1916 May 15, 1988.
Gehrtz and Bjorklund, Quantum-Limited Laser Frequency-Modulation Spectroscopy, J. Opt. Soc. Am. B, vol. 2, No. 9, pp. 1510–1526, Sep. 1985.
Carlisle, Cooper and Preier, Quantum Noise–Limited FM Spectroscopy with a Lead-Salt Diode Laser, Applied Optics, vol. 28, No. 13, pp. 2567–2576, Jul. 1, 1989.
J. Reid, M. El-Sherbiny, B. K. Garside, and E. A. Ballik, Applied Optics Sensitivity Limits of a Tunable Diode Laser Spectrometer, With Application To The Detection of $NO_2$ at the 100–ppt level, pp. 3349–3354.
D. T. Cassidy and J. Reid, Applied Physics B, Harmonic Detection with Tunable Diode Lasers—Two–Tone Modulation, pp. 279–285, 1982.

*Primary Examiner*—Vincent P. McGraw
*Assistant Examiner*—K. P. Hantis
*Attorney, Agent, or Firm*—Bell, Seltzer, Park & Gibson

[57] ABSTRACT

A method and apparatus using a frequency tunable laser to generate a beam which passes through a sample cell and onto an optical detector wherein the tunable laser is modulated at a predetermined frequency which has the undesired effect of producing a periodic interference fringe near an absorption induced signal. An additional level of modulation is applied to the laser beam by a triangular waveform having a predetermined peak-to-peak amplitude and frequency. The triangular waveform peak-to-peak amplitude produces a frequency swing of the laser beam so as to generate from the periodic interference fringe, a signal having reduced components near the absorption induced signal. The signal at the optical detector is demodulated by a lock-in amplifier tuned to a predetermined harmonic of the frequency of the triangular waveform.

20 Claims, 6 Drawing Sheets

METHOD AND APPARATUS FOR REDUCING FRINGE INTERFERENCE IN LASER SPECTROSCOPY

FIELD OF THE INVENTION

The invention relates to the field of spectroscopy, and, more particularly, to a method and apparatus for laser absorption spectroscopy.

BACKGROUND OF THE INVENTION

As a technique for sensitive trace gas detection, laser absorption spectroscopy is attractive because of its simplicity and insensitivity to the environmental conditions of the absorbing species. Tunable diode laser (TDL) spectrometers are particularly suited to high sensitivity studies, in part because they may be frequency modulated to reduce low frequency laser noise and electronic noise. A typical spectrometer includes a frequency tunable laser for generating a laser beam which passes through a sample cell and onto an optical detector. The signal received at the optical detector is demodulated to obtain the absorption induced signal.

Unfortunately, sensitivity is usually severely limited by the presence of interference fringes (etalon fringes) which appear as the narrow bandwidth laser is tuned through the range of the desired absorption signal. See, for example, Carlisle et al., *Quantum Noise-Limited FM Spectroscopy with a Lead-Salt Diode Laser,* Applied Optics, Vol. 28, No. 13, pp. 2567-2576, Jul. 1, 1989. The interference fringes are attributable to laser frequency dependent interference between pairs of parallel optical surfaces through which the laser beam must pass as it propagates from the laser, through the sample cell, and to the optical detector. The fringes may result from laser transmission through individual optical elements, such as windows or lenses, or through air and vacuum paths separated by the surfaces of different system elements. The reflections causing the interference fringes are extremely difficult to eliminate completely even with high quality anti-reflection coatings and careful optical alignment. These fringes, even when very weak, can easily overwhelm the absorption induced signal from the sample.

Attempts have been made in the prior art to reduce the undesirable effects of such interference fringes. For example, U.S. Pat. No. 4,934,816 to Silver et al. discloses a mechanical approach to reducing interference fringes. A piezoelectric transducer translationally vibrates an active optical element, such as a mirror, in the optical path of the tunable laser. The interference fringes are then averaged over time to near zero using a sawtooth (triangle) waveform to drive the piezoelectric transducer that vibrates the optical element, so that each spatial position of the optical element is sampled with equal probability.

The Silver et al. patent also discloses that the fringe averaging effect may be obtained with a detection apparatus employing a lock-in amplifier referenced to the system modulation frequency which is asynchronous with respect to the vibration frequency of the active optical element. The most important consideration in choosing the vibration frequency of the active element is that it be asynchronous with other system frequencies, particularly the lock-in reference frequency, so that fringe averaging can occur. See also Silver and Stanton, *Optical Interference Fringe Reduction in Laser Absorption Experiments,* Applied Optics, Vol. 27, No. 10, pp. 1914-1916, May 15, 1988.

Unfortunately, fast data acquisition cannot be performed with the Silver et al. technique, since averaging for a period longer than the period of the vibration frequency is required. Thus, the Silver et al. patent discloses mechanical modulation of the interference fringe at a very low frequency (less than about 100 Hz). Accordingly, the signal must be integrated to average out the fringes because the fringe signal is translated into very low frequency oscillation at the output of the lock-in amplifier. Moreover, the detection bandwidth of the spectrometer is limited to a very small range.

Another mechanical approach to reducing interference fringes is disclosed in U.S. Pat. No. 4,684,258 to Webster. The Webster patent discloses a Brewster plate spoiler in the laser path downstream of the sample cell and operated by a controller for oscillating the spoiler back and forth about one axis. The oscillating spoiler cyclically varies the optical path length and creates standing waves in a second cavity exterior to the laser's inside cavity. The patent also discloses that for fringe averaging, the Brewster plate is preferably driven by a triangular wave oscillation signal which is several times the frequency of the free spectral range. Unfortunately, such a mechanical approach to fringe reduction is relatively complex, difficult to precisely control, and may not be fully satisfactory for removing unwanted interference fringes. Moreover, the mechanical approach of fringe reduction disclosed in the Webster patent also requires signal integration to average out the fringes, and, therefore, suffers from a limited detection bandwidth.

Other techniques are also known for attempting to reduce interference fringes in laser absorption spectroscopy. For example, an article by Carlisle, et al. *Quantum Noise-Limited FM Spectroscopy with a Lead-Salt Diode Laser,* Applied Optics, Vol. 28, No. 13, pp. 2567-2576, Jul. 1, 1989 discusses a two-tone frequency modulation technique for laser spectroscopy. The technique includes modulating the laser simultaneously at two arbitrary but closely spaced frequencies, and monitoring the beat tone between these two frequencies as the laser carrier and associated sidebands are tuned through a desired absorption line.

In the Carlisle et al. system, a conventional lead-salt diode is driven by superposition of three electrical signals. The signals are a DC current to forward bias the laser diode above threshold, a 1-KHz current ramp to repetitively sweep the laser output frequency across an absorption line of interest, and a two-tone radio frequency signal at a predetermined frequency using two radio frequency synthesizers and a double-balanced mixer. The 1-KHz current ramp and DC bias are adjusted in amplitude so that the output frequency of the laser just sweeps across the absorption line of interest. A low-pass filter is disclosed for removing interference fringes without significantly affecting the two-tone signal. However, if the free spectral range linewidth of the interference fringe is larger than or approximately equal to the absorption linewidth, the suppression of the fringe is severely limited. In addition, baseline noise cannot be eliminated because of the lowpass characteristic of the technique. Further disadvantages of the Carlisle et al. approach include a requirement for current ramping, and the requirement for a relatively complicated linear phase filter for recovering the absorption induced signal. The approach is also not applicable when line locking is needed.

Other techniques using multiple beams are also known in the art. An article by Gehrtz et al., *Quantum-Limited Laser Frequency-Modulation Spectroscopy*, J. Opt. Soc. Am. B, Vol. 2, No. 9, pp. 1510-1526, September, 1985, describes frequency modulation spectroscopy including the difficulties associated therewith. In particular, the article discloses reduction of the residual amplitude modulation of the tunable laser by, for example, techniques using double laser beams.

An article by Cassidy et al. entitled *Harmonic Detection with Tunable Diode Lasers—Two-Tone Modulation*, Applied Physics, B 29, 279-285 (1982), discloses two-tone modulation to improve the sensitivity of tunable diode laser absorption spectrometers. A sinusoidal jitter modulation is applied having a predetermined phase and frequency to simultaneously minimize the fringe signal and increase the harmonic absorption induced signal. Unfortunately, the fringe reduction technique is essentially lowpass in nature. Moreover, as in the mechanical approaches described above, the Cassidy et al. approach requires that the signal must be integrated to average out the fringes, and, therefore, a low detection bandwidth results.

An article by Reid et al. entitled *Sensitivity Limits of a Tunable Diode Laser Spectrometer, with Application to the Detection of $NO_2$ at the 100-ppt Level*, Applied Optics, Vol. 19, No. 19, pp. 3349-3354 (October, 1980) discloses that minima of interference fringes occur when the amplitude of the sinusoidal modulation of the tunable diode laser is exactly an integral number of the interference fringe spacings. The article discloses that jitter modulation of a symmetric sawtooth at a frequency of 300-500 Hz and an amplitude much smaller than the 3 KHz sinusoidal modulation used for the second harmonic detection can be used to sweep the diode laser wavelength back and forth over exactly one fringe. This sweep occurs many times during an integration period of the lock-in amplifier set to the second harmonic (6 KHz) of the sinusoidal modulation, and hence the fringes are electronically washed out. The small amplitude of the jitter modulation ensures that is has little effect on the $NO_2$ second harmonic absorption line shape. As in several of the mechanical and electronic approaches outlined above, the Reid et al. technique requires integration and hence has a low detection bandwidth.

SUMMARY OF THE INVENTION

It is therefore an object of the invention to provide a method and apparatus for conducting laser spectroscopy that substantially reduces an unwanted interference fringe to thereby increase measurement sensitivity.

It is another object of the invention to provide a method and apparatus for conducting laser spectroscopy that operates over a wide range of ratios of the absorption signal linewidth to interference fringe free spectral range.

It is yet another object of the invention to provide a method and apparatus for conducting laser spectroscopy that has a wide detection bandwidth and that does not require integration to average out an interference fringe.

A conventional laser spectrometer includes a frequency tunable laser, modulated at a predetermined frequency, and aligned to pass its output laser beam through a sample and to an optical detector. The modulation at the predetermined frequency may have the typical yet undesired effect of generating a periodic interference fringe signal near the absorption induced signal. The present invention provides a method and apparatus for interference fringe reduction for high resolution, high sensitivity, laser absorption spectroscopy by further modulating the tunable laser with a triangular waveform having a predetermined peak-to-peak amplitude and a predetermined frequency.

A triangular waveform generator, coupled to the modulator of the tunable laser, causes a frequency swing of the laser beam from the tunable laser sufficient to produce from the periodic interference fringe a signal having reduced components near a non-periodic absorption induced signal. The signal from the optical detector is then demodulated at a predetermined harmonic of the triangular waveform frequency to obtain the absorption induced signal. Thus, the signal-to-background ratio of the absorption induced signal is enhanced. The predetermined frequency of the laser beam may also be scanned relatively slowly over a range to obtain a spectrum including the absorption induced signal.

In one embodiment according to the invention, when the difference between the interference fringe free spectral range and the absorption induced signal linewidth is about one order of magnitude or less, the predetermined peak-to-peak amplitude of the triangular waveform is selected to generate a frequency swing of the laser beam substantially equal to $(n+\frac{1}{2})$ times the free spectral range frequency of the interference fringe, wherein n is a positive integer. The modulation theoretically causes the periodic interference fringes to go to zero. Then the signal received at the optical detector can be demodulated by a lock-in amplifier set to an odd harmonic of the triangular waveform frequency, such as the triangular waveform fundamental frequency.

The triangular waveform peak-to-peak amplitude may also be selected to generate a predetermined frequency swing of the laser beam substantially equal to a positive integer times the free spectral range frequency of the interference fringe also when the difference between the interference fringe free spectral range and the absorption induced signal is about one order of magnitude or less. In this case, the received signal is preferably demodulated by a lock-in amplifier set at an even harmonic of the triangular waveform predetermined frequency, such as the second harmonic.

In another embodiment of the invention, the predetermined peak-to-peak amplitude of the triangular waveform is selected to produce a frequency swing of the laser beam to maximize the absorption induced signal. For this embodiment, the received signal is demodulated by a lock-in amplifier set at a predetermined harmonic of the triangular waveform frequency when the difference between the free spectral range of the interference fringe and the spectral linewidth of the absorption induced signal is greater than about two orders of magnitude. If the difference between the free spectral range of the interference fringe and the spectral linewidth of the absorption induced signal is between about one to two orders of magnitude, the received signal is preferably demodulated at the second harmonic or a higher harmonic of the triangular waveform frequency, such as the second harmonic. Proper selection of the peak-to-peak amplitude of the triangular waveform can greatly reduce the interference fringe even when the interference fringe free spectral range and absorption signal linewidth are very close.

The invention uses a modulation scheme which effectively reduces the periodic interference fringe while preserving the desired non-periodic absorption signal. The invention is a bandpass rather than lowpass method and is able to accommodate a wide range of interference fringe free spectral range to absorption signal linewidths. The invention also effectively rejects any residual amplitude modulation present on the laser beam without requiring the need for baseline nulling or careful adjustment of the radio frequency phase signal at the radio frequency mixer. While frequency modulation spectroscopy is described in detail herein, it would be readily understood by those skilled in the art the invention may also be readily adapted to be used in conjunction with conventional wavelength modulation laser spectroscopy, for example.

DESCRIPTION OF THE PREFERRED EMBODIMENTS

The present invention will now be described more fully hereinafter with reference to the accompanying drawings and illustrative examples, in which preferred embodiments of the invention are shown. This invention may, however, be embodied in many different forms and should not be construed as limited to the embodiments set forth herein. Rather, applicants provide these embodiments so that this disclosure will be thorough and complete, and will fully convey the scope of the invention to those skilled in the art. Like numbers refer to like elements throughout.

Figure 1:
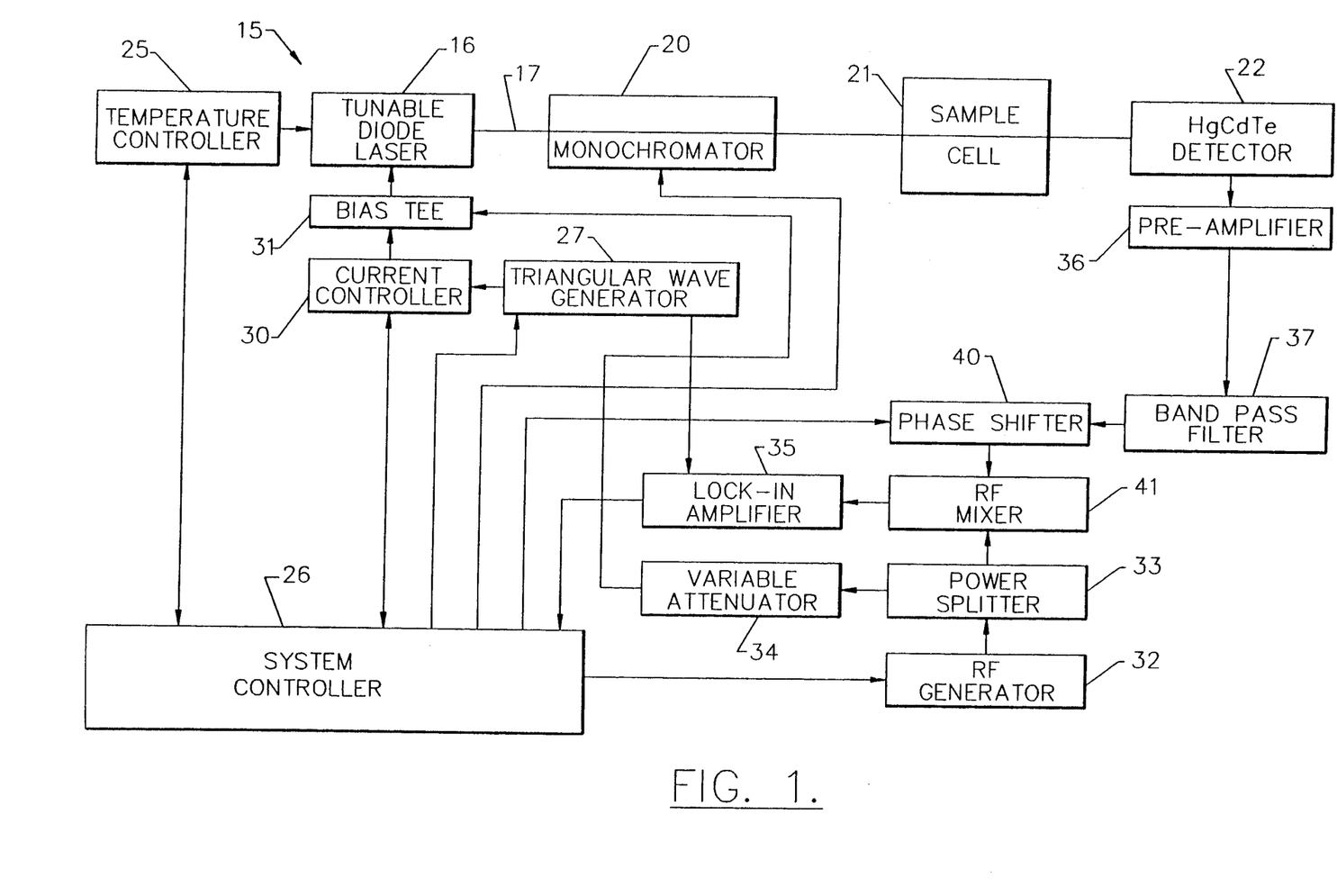
FIG. 1 is a schematic diagram of the laser absorption spectrometer according to the present invention.

There is shown in FIG. 1 a laser absorption spectrometer according to the invention generally designated by reference numeral 15. The spectrometer 15 includes a tunable diode laser 16 for generating a laser beam 17 which passes through a mode selection monochromator 20, through a gas sample contained within a sample cell 21, and onto an optical detector 22. The tunable laser diode 16 may be a conventional tunable laser of the type available from Laser Photonics Inc., Orlando, Fla. The optical detector 22 may be a conventional photovoltaic HgCdTe detector of the type available from New England Research, Sudbury, Mass.

The tunable diode laser 16 is temperature compensated by a temperature controller 25 which is also interfaced to the spectrometer controller 26. The spectrometer controller 26 preferably is a programmable computer that may also interface to other components, such as through conventional stepper motors for example, as would be readily understood by those skilled in the art.

The spectrometer controller 26 may be adapted to slowly sweep the frequency of the tunable laser 16 over a spectrum of frequencies including the frequency of the desired absorption signal.

The frequency of the tunable laser 16 is readily controlled through control of the injection current. A triangular waveform generator 27 operated at a predetermined frequency and with a predetermined peak-to-peak amplitude provides a second level of modulation to the tunable laser 16, as more fully described below in the detailed description of the method according to the invention. The triangular waveform generator 27 feeds the current controller 30 which in turn feeds a bias tee 31 to modulate the tunable laser 16. The bias tee 31 also receives an input from the radio frequency (RF) generator 32, via the power splitter 33 and variable attenuator 34. The bias tee 31 may be of the type available from Triangle Microwave, East Hanover, N.J. under the Model Number EP-18. The RF generator 32 may be of the type available from Hewlett Packard, Paramus, N.J. under the Model Number HP8565B.

The demodulator portion of the spectrometer 15 includes a pre-amplifier 36 coupled to the optical detector 22. The signal from the pre-amplifier 36 is fed through a bandpass filter 37 and a controllable phase shifter 40 to the RF mixer 41. The phase shifter 40 is preferably of the type available from Merimac Industries Inc., West Caldwell, N.J. offered under the Model Number PEW-3-30. The RF mixer 41 may preferably be a Model Number M6F offered by Watkins-Johnson Company, Palo Alto, Calif. The operation of the spectrometer 15 including the proper selection of the triangular waveform peak-to-peak amplitude and frequency produced by the triangular waveform generator 27, as well as coordination with the lock-in amplifier 35, is described below with reference to the method according to the invention.

The method according to the present invention allows selective rejection of etalon-like fringe signals while preserving the true absorption induced signal in laser absorption spectroscopy. In a typical sensitive laser spectroscopy detection experiment, frequency modulation spectroscopy (FMS) is used as the primary means of rejecting low frequency laser and electronic noise. See, for example, G. C. Bjorkland, "Frequency-Modulation Spectroscopy: A New Method for Measuring Weak Absorptions and Dispersions," Opt. Let. Vol. 5, p. 15 (1980), and Gehrtz et al., *Quantum-Limited Laser Frequency-Modulation Spectroscopy*, J. Opt. Soc. Am. B, Vol. 2, No. 9, pp. 1510–1526, September, 1985. Thus, the tunable laser is modulated at a predetermined frequency which may have the undesired effect of generating an interference fringe.

Using FMS, the absorption induced signal is proportional to the derivative of the optical transmission function of the sample gas and any intervening interference fringes. Assuming for simplicity only one such interference fringe, the demodulated FM signal is proportional to $A'(\nu)$, given by:

$$A'(\nu) = V'(\nu) + A_e'(\nu) + RAM(\nu) \qquad (1)$$

where $\nu$ is the optical frequency of the laser beam. $V(\nu)$ is the Voigt profile of a typical absorption peak and $A_e(\nu)$ is the false absorption signal arising from the interference fringe. As would be readily understood by those skilled in the art, the Voigt profile includes contributions from two components: (1) a homogenous linewidth contribution caused as the atoms or molecules are excited and then relax; and (2) a gas velocity, or doppler shift, contribution. RAM($\nu$) represents any additional residual amplitude modulation present on the laser beam and is an artifact of FMS. The primes indicate differentiation with respect to $\nu$. For some of the results presented below, the absorption induced signal linewidth will be narrow enough that the FMS signal will not be a true derivative in which case a more complicated expression would replace V'($\nu$). This change will be made implicitly when necessary.

Modeling the interference fringe as a pair of surfaces with intensity reflectivity R, $A_e(\nu)$ is given by:

$$A_e(\nu) = \frac{4R\sin^2\left(\frac{\pi\nu}{\nu_e}\right)}{(1-R)^2 + 4R\sin^2\left(\frac{\pi\nu}{\nu_e}\right)} \quad (2)$$

where $\nu_e$ is the free spectral range (FSR) of the etalon. Where R is small, Eq. 2 can be written as:

$$A_e(\nu) = 2R\left(1 - \cos\left(\frac{2\pi\nu}{\nu_e}\right)\right) \quad (3)$$

and the first derivative becomes:

$$A'_e(\nu) = \frac{4\pi R}{\nu_e}\sin\left(\frac{2\pi\nu}{\nu_e}\right) \quad (4)$$

This form will be used in Eq. 1.

Since R is normally larger than $1\times10^{-3}$ even for high quality anti-reflection coated surfaces, the absorption signal arising from a trace gas of optical density less than $1\times10^{-5}$ can easily be overwhelmed by the interference fringe. The method according to the invention generates a Fourier expansion of the signal by applying an additional level of modulation to the high frequency modulated laser. In particular, by modulating $\nu$ with a symmetric triangular waveform $T(\omega,t)$ with a predetermined peak-to-peak amplitude and a predetermined frequency, $\nu$ and A'($\nu$) transform to:

$$\nu \to \nu_c + \nu_s T(\omega,t) \text{ and } A'(\nu) \to A'(\nu_c,t) \quad (5)$$

where $\omega$ is the frequency of the triangular wave and $\nu_s$ is the frequency swing or peak-to-peak value of the overall triangular waveform. The frequency $\nu_c$ is the laser center frequency. A spectrum may be obtained by slowly varying $\nu_c$ while simultaneously modulating the laser as described above. A'($\nu_c$,t) is thus made a symmetric function of t and may be expressed as a cosine series:

$$A'(\nu_c, t) = \sum_{n=0} (V_n(\nu_c) + A'_{en}(\nu_c) + RAM_n(\nu_c))\cos(n\omega t) \quad (6)$$

The Fourier coefficients for this expression may be evaluated by integrating A'($\nu_c$,t)cos(n$\omega$t) over one full period 1/$\omega$, but the integration can be simplified by recognizing that during alternate half cycles the integration over t may be replaced with an integration over $\nu$ since during that interval the mapping (remapping) may be written explicitly as:

$$\nu = \nu_c \pm \nu_s \omega t \quad (7)$$

where $\pm$ refers to the rising and falling half cycle of the triangular waveform, respectively. The integrals for the Fourier coefficients may then be written as:

$$V_n(\nu_c) = \frac{2}{\nu_s}\int_{\nu_c + \frac{\nu_s}{2}}^{\nu_c - \frac{\nu_s}{2}} V(\nu)\cos\left(\eta\pi\frac{\left(\nu - (\nu_c - \frac{\nu_s}{2})\right)}{\nu_s}\right)d\nu \quad (8)$$

$$A'_{en}(\nu_c) = \quad (9)$$

$$\frac{2}{\nu_s}\int_{\nu_c - \frac{\nu_s}{2}}^{\nu_c + \frac{\nu_s}{2}} A'_e(\nu)\cos\left(\eta\pi\frac{\left(\nu - (\nu_c - \frac{\nu_s}{2})\right)}{\nu_s}\right)d\nu$$

Assume that RAM($\nu$) varies slowly with $\nu$ so that $RAM_n$ is zero for n greater than 1. Both $V'_n$ and $A'_{en}$ are independent of $\omega$ in the system provided $\omega$ is small compared to all the other frequencies.

To explore the effect of the Fourier expansion on the signal amplitudes, two dimensionless parameters $$X_e = \frac{\nu_s}{\nu_e} \text{ and } X_\Gamma = \frac{\nu_s}{\Gamma}$$

are introduced which respectively define the $n^{th}$ order Etalon Fringe Multiplication Ratio $EFMR_n$ ($X_e$) and $n^{th}$ order Absorption Signal Reduction Ratio $ASRR_n(X_r)$ as:

$$EFMR_n(X_e) = \frac{\text{peak-to-peak value of } A'_{en}}{\text{peak-to-peak value of } A'_e} \quad (10)$$

and $$ASRR_n(X_\Gamma) = \frac{\text{peak value of } V_n}{\text{peak value of } V'} \quad (11)$$

where 'peak-to-peak' refers to the amplitude of the periodic interference fringes as a function of $\nu_c$ and 'peak value' is the maximum of the true absorption induced signal and $\Gamma$ is the absorption induced signal linewidth. These functions may be evaluated using Eqs. 8 and 9.

Figure 2:
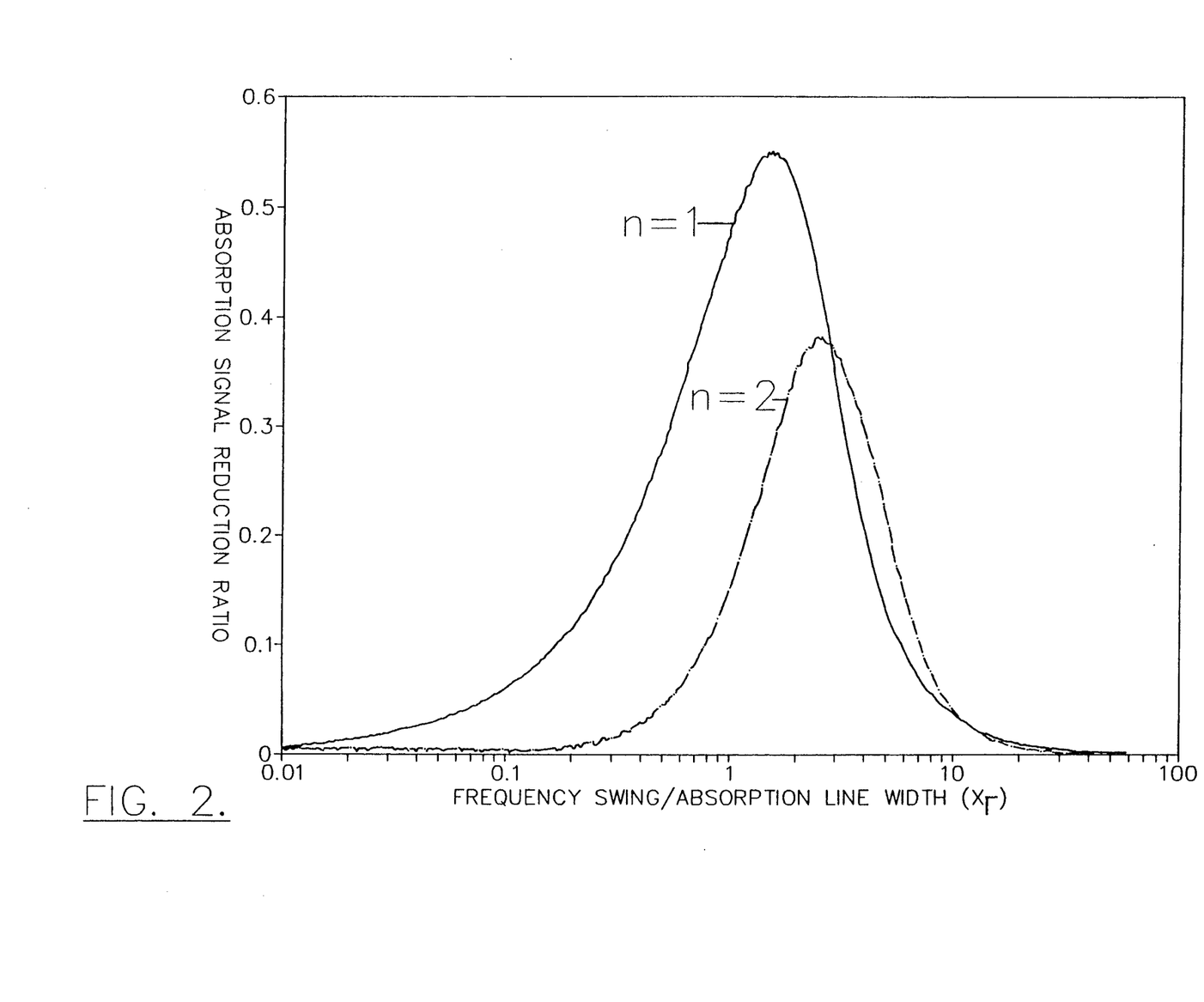
FIG. 2 is a graph of the Etalon Fringe Multiplication Ratio for first and second order calculated waveforms according to the invention.
Figure 3:
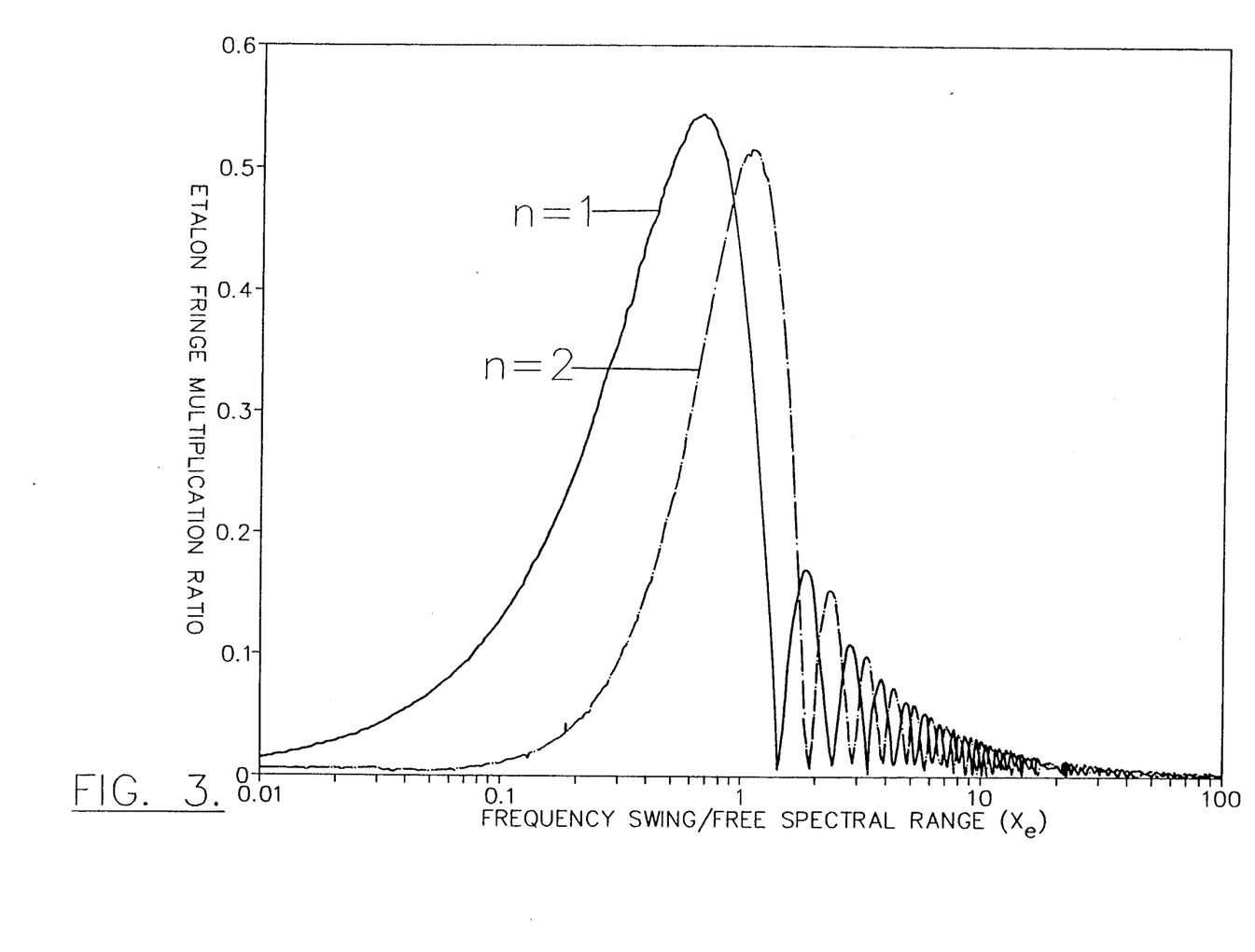
FIG. 3 is a graph of the Absorption Signal Reduction Ratio for first and second order calculated waveforms according to the invention.

With reference to the two calculated waveforms for $EFMR_n$ ($X_e$) shown in FIG. 2 for n=1 (fundamental or first harmonic) and n=2 (second harmonic), each of the waveforms rise monotonically as $X_e$ increases, reaching an absolute maximum at $X_e$=0.681 and 1.14, respectively. As $X_e$ increases further, gradually decreasing maxima occur at periodic intervals. Of particular interest is the fact the $EFMR_n$ ($X_e$) analytically goes to zero at $X_e$=m+$\frac{1}{2}$ for n=an odd integer (odd harmonics) and at $X_e$=m, for n =an even integer (even harmonics), where m is a positive integer. Stated in other words, as the laser makes its linear scan through the periodic interference fringe with frequency $\omega$, the resultant waveform will have no periodic component at n$\omega$ for these precise values of $X_e$. Moreover, since the true absorption induced signal is not periodic, no zeroes occur as a result of the modulation. FIG. 3 shows $ASRR_n(X_\Gamma)$ for n = 1 and n = 2. The waveforms peak at an n dependent value of $X_\Gamma$ near unity and fall off monotonically on either side.

Both FIGS. 2 and 3 illustrate the bandpass nature of the method of the invention which selects signals having a spectral bandwidth the same order of magnitude as $\nu_s$. The rejection passband for $EFMR_n(X_e)$ becomes narrower as n increases.

Proper choice of $\nu_s$ for maximum fringe reduction according to the invention depends on the size of $\Gamma$ relative to $\nu_e$. When the two frequencies differ by more than two orders of magnitude, $\nu_s$ is chosen to maximize the absorption induced signal, and this choice automatically minimizes the interference fringe for either the n=1 or n=2, or any predetermined harmonic absorption induced signal components. With only one order of magnitude difference between $\Gamma$ relative to $\nu_s$, it is still possible to use the n=2 and other higher harmonic components to maximize the absorption signal and minimize the interference fringe. Precise adjustment of $\nu_s$, such as setting the frequency swing so that $X_e = m + \frac{1}{2}$ for n = an odd integer or at $X_e = m$ for n = an even integer as described above, should still be able to substantially reduce the interference under most circumstances even when both frequencies are comparable.

The following examples are provided to further illustrate the invention, and are not to be construed as limiting thereof.

EXAMPLE 1

To demonstrate the method and apparatus according to the invention, an experiment was conducted using a tunable lead salt diode laser 16 Model Number L5615-880 available from Laser Photonics and tuned to a frequency of 872 cm$^{-1}$. The laser is easily frequency modulated through control of the injection current. The triangular waveform modulation was applied to the laser mixed with a 40 MHz RF signal for FMS.

The modulated laser beam 17 was passed through a 1.445 GHz free spectral range solid germanium etalon and then detected on a HgCdTe photovoltaic detector 22 Model Number MPV11-0.50-B60 available from New England Research. The photocurrent from the optical detector 22 was first demodulated at 40 MHz using an RF mixer 41 and then lock-in detected at the triangle waveform fundamental frequency (n=1) or its second harmonic (n=2). For these measurements, the triangular waveform frequency was set to a frequency of 6 KHz. The value of $\nu_s$ was determined using the laser tuning rate and with the measured amplitude of the triangular waveform detected from the current controller 30 for the laser. Spectra for the experiments were obtained by slowly scanning the laser frequency $\nu_c$ over a 4 GHz range in a time of 16 seconds.

Figure 4:
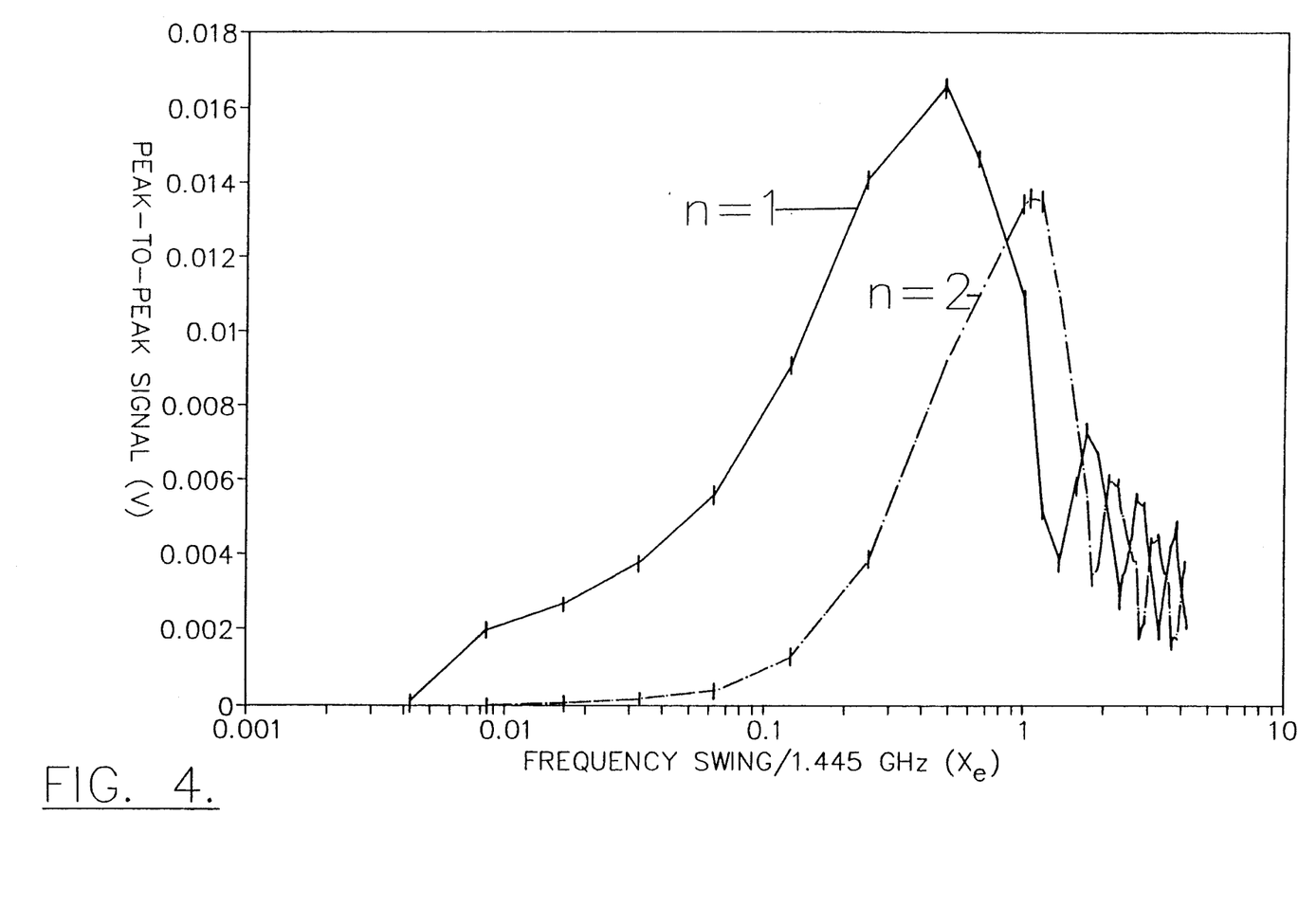
FIG. 4 is a graph of measured first and second order peak-to-peak absorption signals corresponding to Example 1 according to the invention.

The peak-to-peak signal for the germanium etalon was recorded as a function of $X_e$. FIG. 4 shows the measured data obtained for n=1 and n=2. As the intensity reflectivity (R) for the germanium etalon was about 0.36, $A_e$ is not purely sinusoidal and as a result $EFMR_n(X_e)$ does not go exactly to zero but the general shape is similar to the calculated expression.

EXAMPLE 2

Figure 5:
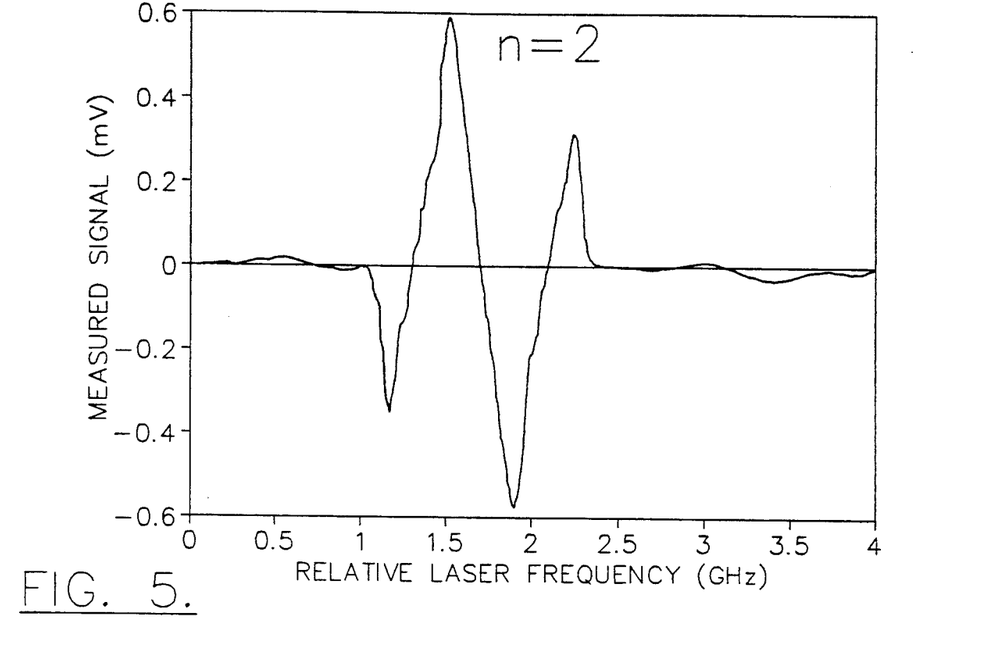
FIGS. 5 and 6 are graphs of measured spectrums corresponding to Example 2 according to the invention.
Figure 6:
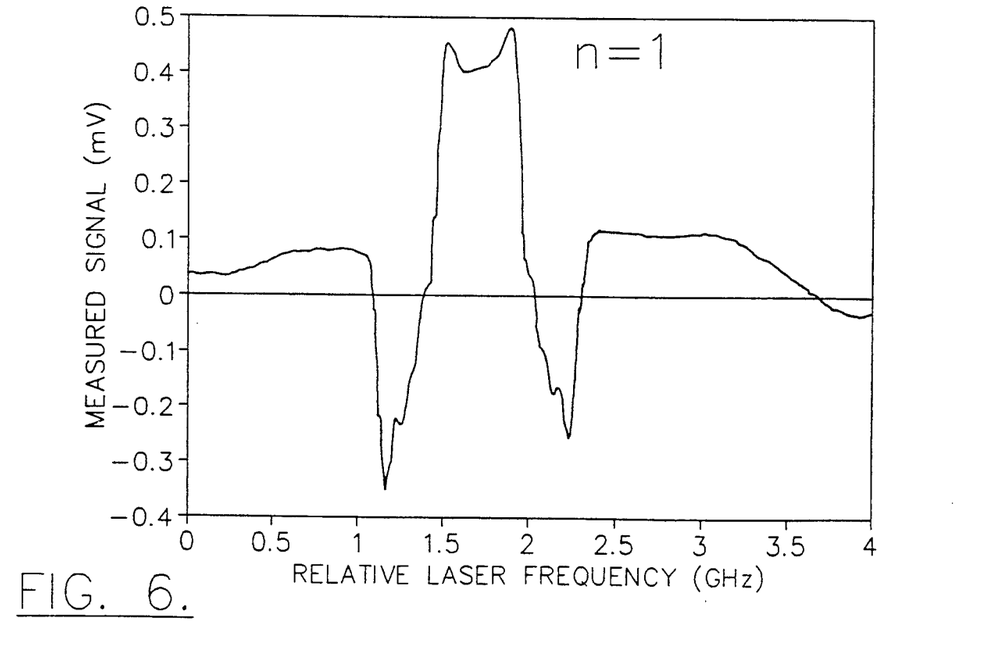

To demonstrate the effectiveness of the invention for reducing fringe interference in a realistic sensitive detection measurement, the absorption spectrum of carbonyl sulfide (OCS) was measured. The R(32) line of the first rotational series of OCS ($\nu_o$=871.6693 cm$^{-1}$) was investigated. A sample of 1% OCS in a helium (He) certified gas mixture was used. FIGS. 5 and 6 show measured spectral data for an OCS partial pressure of 2.73 mTorr and total path length of 42.2 cm, corresponding to a calculated absorbance of $1.3 \times 10^{-3}$. The sample gas is predominantly doppler broadened at this pressure. The parameter $\nu_s$ was set to 1 GHz roughly corresponding to $X_\Gamma = 24$.

In FIG. 5, the n=2 measured spectrum is plotted and in addition to the OCS absorption line, weak 660 MHz free spectral range interference fringes are clearly visible. The beam was carefully aligned to eliminate fringes from the vacuum chamber and it is believed that the observed interference fringes were due to internal reflection in the mode selection monochromator. The interference fringe is estimated to be approximately equivalent to an absorbance of $5 \times 10^{-5}$. Since $X_e = 1.5$ for these fringes, it was expected that the n=1 signal would be in the first null point of FIG. 2 and this effect is demonstrated in the measured spectrum plotted i FIG. 6. The measured spectrum of FIG. 6 also demonstrates clearly that $RAM_1$ is non-zero and is weakly laser frequency dependent, but that $RAM_2$ is zero as assumed in the theoretical analysis.

EXAMPLE 3

To further demonstrate the effectiveness of the invention for interference fringe reduction, the OCS partial pressure was reduced to 84 $\nu$Torr for a second measurement scan, resulting in a purely doppler broadened linewidth of 40 MHz and an absorbance of $5 \times 10^{-5}$. To maximize the absorption induced signal, $\nu_s$ was adjusted to 100 MHz, resulting in $X_\Gamma = 2.5$ and $X_e = 0.152$, thereby placing the experiment in the small $X_e$ limit of FIG. 2 for n=2. Also, for such a narrow linewidth, the FMS signal line shape is no longer derivative-like, instead resulting in a somewhat more complicated signature for the OCS absorption signal.

Figure 7:
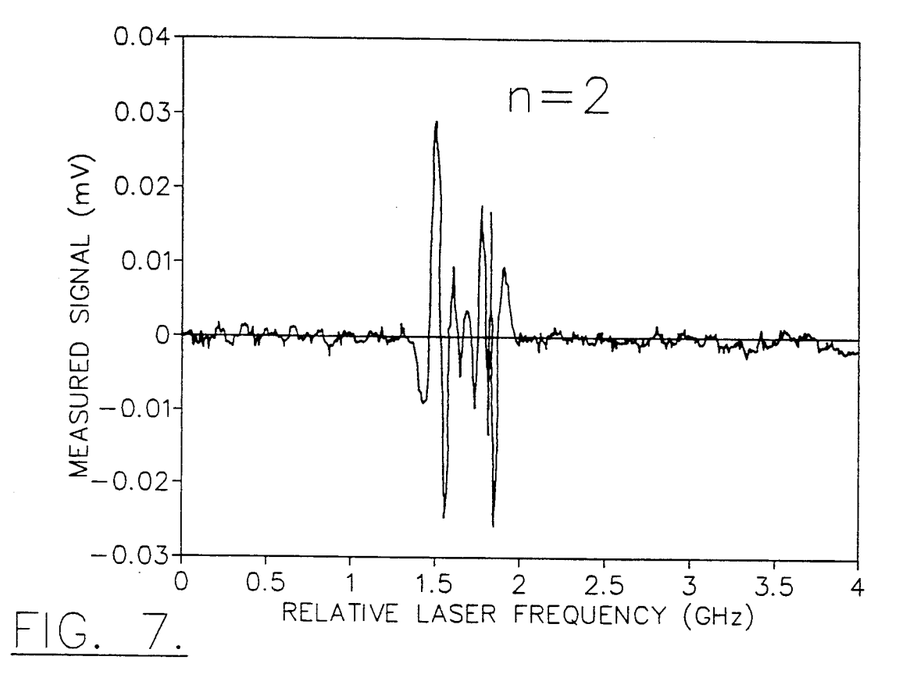
FIGS. 7 and 8 are graphs of measured spectrums corresponding to Example 3 according to the invention.
Figure 8:
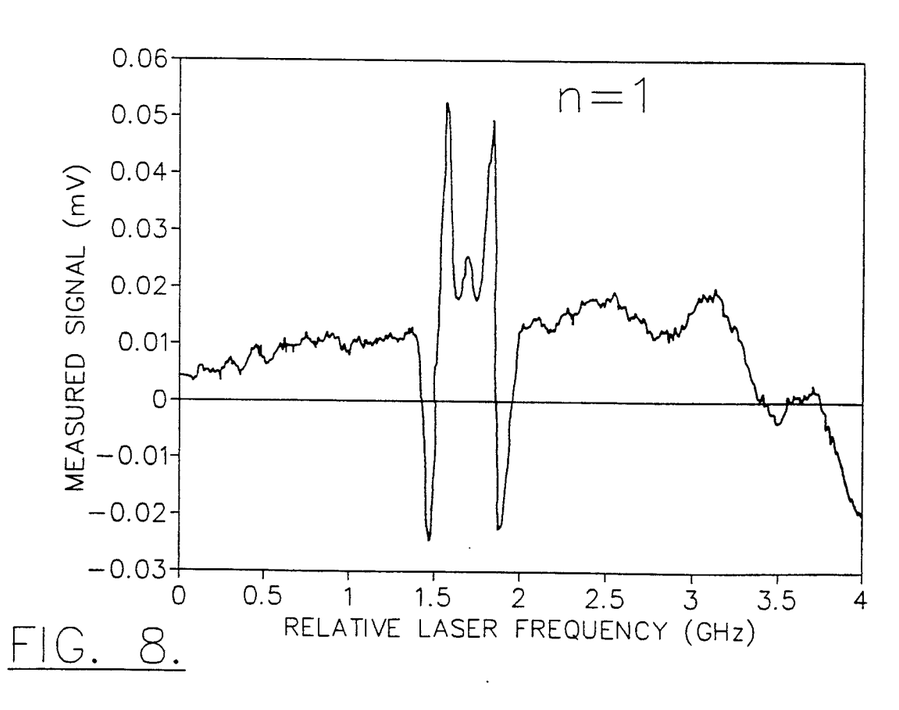

In FIG. 7, the n=2 measured spectrum is plotted. The interference fringes are suppressed below the noise floor and there is no RAM-induced baseline shift. The n=1 data are plotted in FIG. 8 and while visible, the interference fringes are much reduced in accordance with FIG. 2. The absorbance equivalent noise in FIG. 7 is $3 \times 10^{-6}$.

In summary, the present invention provides a method and apparatus for interference fringe rejection for high resolution, high sensitivity laser absorption spectroscopy. The invention uses a modulation scheme which effectively nulls a periodic interference fringe while preserving the desired absorption induced signal. The apparatus and method according to the invention may be used in diagnostic equipment which uses laser absorption spectroscopy. For example, the invention may be used to provide sensitive diagnostics for gas phase materials processing reactors, such as those used for semiconductor fabrication and processing. While the invention is well suited to reduce a single periodic interference fringe, it may also be used when there is more than one fringe at the desired scanning frequency. Stated in other words, if the signal received at the detector contains contributions from more than one fringe, nevertheless, the wide dynamic range of the invention permits at least finding an optimum setting which would provide an improved signal-to-background ratio over what would be obtained without using the invention. The present invention also provides an effective way to reject laser RAM without requiring the need for baseline nulling or careful adjustment of the RF phase signal at the RF mixer.

While frequency modulation spectroscopy is described in detail herein, it would be readily understood by those skilled in the art the invention may be used in conjunction with conventional wavelength modulation, for example. Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A method for reducing fringe interference in laser absorption spectroscopy using a frequency tunable laser aligned to pass a laser beam through a sample volume and to an optical detector to thereby detect an absorption induced signal from the sample, said method comprising the steps of:

modulating the tunable laser at a first predetermined frequency having the undesired effect of generating a periodic interference fringe near the absorption induced signal;

modulating the tunable laser with a triangular waveform having a predetermined peak-to-peak amplitude and a second predetermined frequency different from said first predetermined frequency, the predetermined peak-to-peak amplitude of the triangular waveform being selected to generate a frequency swing of the laser beam sufficient to produce from the periodic interference fringe a signal having reduced components near an absorption induced signal; and demodulating the signal received by the optical detector at a predetermined harmonic of the second predetermined frequency of the triangular waveform;

whereby the signal-to-background ratio of the absorption induced signal is enhanced.

2. The method according to claim 1 further comprising the step of determining the difference between the free spectral range of the interference fringe and the spectral linewidth of the absorption induced signal; wherein the predetermined peak-to-peak amplitude of the triangular waveform is selected to generate a frequency swing of the laser beam substantially equal to $(n+\frac{1}{2})$ times the free spectral range frequency of the interference fringe when the difference between the free spectral range of the interference fringe and the absorption induced signal linewidth is about one order of magnitude or less; and wherein n is a positive integer.

3. The method according to claim 2 wherein the step of demodulating the signal received at the optical detector comprises the step of demodulating the signal at an odd harmonic of the second predetermined frequency of the triangular waveform.

4. The method according to claim 1 further comprising the step of determining the difference between the free spectral range of the interference fringe and the spectral linewidth of the absorption induced signal; and wherein the predetermined peak-to-peak amplitude of the triangular waveform is selected to generate a predetermined frequency swing of the laser beam substantially equal to a positive integer times the free spectral range frequency of the interference fringe when the difference between the free spectral range of the interference fringe and the absorption induced signal linewidth is about one order of magnitude or less.

5. The method according to claim 4 wherein the step of demodulating the signal received at the optical detector comprises the step of demodulating the signal at an even harmonic of the second predetermined frequency of the triangular waveform.

6. The method according to claim 1 wherein the predetermined peak-to-peak amplitude of the triangular waveform is selected to produce a frequency swing of the laser beam to maximize the absorption induced signal.

7. The method according to claim 6 further comprising the step of determining the difference between the free spectral range of the interference fringe and the spectral linewidth of the absorption induced signal; and wherein the step of demodulating the signal received by the optical detector comprises the step of demodulating the signal at the second harmonic or a higher harmonic of the second predetermined frequency of the triangular waveform when the difference between the free spectral range of the interference fringe and the spectral linewidth of the absorption induced signal is in the range of about one order of magnitude to two orders of magnitude.

8. A method for reducing fringe interference in laser absorption spectroscopy using a frequency tunable laser aligned to pass a laser beam through a sample volume and to an optical detector to thereby detect an absorption induced signal from the sample, said method comprising the steps of:

modulating the tunable laser at a first predetermined frequency having the undesired effect of generating a periodic interference fringe near the absorption induced signal;

sweeping the first predetermined frequency of the tunable laser relatively slowly over a predetermined range to obtain a spectrum including the absorption induced signal;

modulating the tunable laser with a triangular waveform having a predetermined peak-to-peak amplitude and a second predetermined frequency different from said first predetermined frequency, the predetermined peak-to-peak amplitude of the triangular waveform being selected to generate a frequency swing of the laser beam sufficient to produce from the periodic interference fringe a signal having reduced components near an absorption induced signal; and demodulating the signal received by the optical detector at a predetermined harmonic of the second predetermined frequency of the triangular waveform;

whereby the signal-to-background ratio of the absorption induced signal is enhanced.

9. The method according to claim 8 further comprising the step of determining the difference between the free spectral range of the interference fringe and the spectral linewidth of the absorption induced signal; wherein the predetermined peak-to-peak amplitude of the triangular waveform is selected to generate a frequency swing of the laser beam substantially equal to $(n+\frac{1}{2})$ times the free spectral range frequency of the interference fringe when the difference between the free spectral range of the interference fringe and the absorption induced signal linewidth is about one order of magnitude or less; and wherein n is a positive integer.

10. The method according to claim 9 wherein the step of demodulating the signal received at the optical detector comprises the step of demodulating the signal at an odd harmonic of the second predetermined frequency of the triangular waveform.

11. The method according to claim 8 further comprising the step of determining the difference between the free spectral range of the interference fringe and the spectral linewidth of the absorption induced signal; and wherein the predetermined peak-to-peak amplitude of the triangular waveform is selected to generate a predetermined frequency swing of the laser beam substantially equal to a positive integer times the free spectral range frequency of the interference fringe when the difference between the free spectral range of the interference fringe and the absorption induced signal linewidth is about one order of magnitude or less.

12. The method according to claim 11 wherein the step of demodulating the signal received at the optical detector comprises the step of demodulating the signal at an even harmonic of the second predetermined frequency of the triangular waveform.

13. The method according to claim 8 wherein the predetermined peak-to-peak amplitude of the triangular waveform is selected to produce a frequency swing of the laser beam to maximize the absorption induced signal.

14. The method according to claim 13 further comprising the step of determining the difference between the free spectral range of the interference fringe and the spectral linewidth of the absorption induced signal; and wherein the step of demodulating the signal received by the optical detector comprises the step of demodulating the signal at the second harmonic or a higher harmonic of the second predetermined frequency of the triangular waveform when the difference between the free spectral range of the interference fringe and the spectral linewidth of the absorption induced signal is in the range of about one order of magnitude to two orders of magnitude.

15. A laser spectrometer for detecting and absorption induced signal from a sample, said spectrometer comprising:
 a frequency tunable laser for generating a laser beam;
 an optical detector positioned in the optical path of the laser beam;
 a cell for containing a sample, said cell positioned in the optical path of the laser beam between said frequency tunable laser and said optical detector;
 a modulator coupled to said frequency tunable laser for modulating same at a first predetermined frequency and having the undesired effect of generating a periodic fringe near an absorption induced signal;
 a triangular waveform generator cooperating with said modulator for further modulating said frequency tunable laser with a triangular waveform having a predetermined peak-to-peak amplitude and a second predetermined frequency different from said first predetermined frequency, said predetermined peak-to-peak amplitude of said triangular waveform producing a frequency swing of said laser beam so as to generate from the periodic interference fringe a signal having reduced components near the absorption induced signal of the sample; and
 a demodulator coupled to said optical detector for obtaining the absorption induced signal, said demodulator including a lock-in amplifier tuned to a predetermined harmonic of said second predetermined frequency of said triangular waveform.

16. The laser spectrometer according to claim 15 wherein said triangular waveform generator includes means for generating a predetermined peak-to-peak amplitude of said triangular waveform so as to produce a frequency swing of the laser beam substantially equal to $(n+\frac{1}{2})$ times the free spectral range frequency of the periodic interference fringe; wherein n is a positive integer; and wherein said lock-in amplifier is tuned to an odd harmonic of the second predetermined frequency of said triangular waveform.

17. The laser spectrometer according to claim 15 wherein said triangular waveform generator includes means for generating a predetermined peak-to-peak amplitude of said triangular waveform so as to produce a frequency swing of said laser beam substantially equal to a positive integer times the free spectral range frequency of the periodic interference fringe; and wherein said demodulator includes a lock-in amplifier tuned to an even harmonic of the second predetermined frequency of said triangular waveform.

18. The laser spectrometer according to claim 15 wherein said triangular waveform generator includes means for generating a predetermined peak-to-peak amplitude of said triangular waveform so as to maximize the absorption induced signal.

19. The laser spectrometer according to claim 18 wherein said lock-in amplifier is tuned to the second harmonic or a higher harmonic of the second predetermined frequency of the triangular waveform when a difference between the free spectral range of the interference fringe and the spectral linewidth of the absorption induced signal is in the range of about one order of magnitude to two orders of magnitude.

20. The laser spectrometer according to claim 15 further comprising a controller cooperating with said modulator for slowly sweeping the first predetermined frequency of said laser beam over a range to obtain a spectrum including the absorption induced signal.

* * * * *